United States Patent [19]
Miyagi

[11] Patent Number: 5,179,935
[45] Date of Patent: Jan. 19, 1993

[54] ENDOSCOPE PROVIDED IN THE INSERTABLE SECTION WITH A FLEXIBLE PART WHICH CAN BE MADE LINEAR

[75] Inventor: Takayasu Miyagi, Hachioji, Japan

[73] Assignee: Olympus Optical Co., Ltd., Tokyo, Japan

[21] Appl. No.: 656,652

[22] Filed: Feb. 19, 1991

[30] Foreign Application Priority Data

May 17, 1990 [JP] Japan ................................ 2-129836
Nov. 28, 1990 [JP] Japan ................................ 2-331921

[51] Int. Cl.⁵ ............................................. A61B 1/06
[52] U.S. Cl. ................................................ 128/4; 128/6
[58] Field of Search .......................... 128/4, 6, 10, 11

[56] References Cited

U.S. PATENT DOCUMENTS

| 4,290,421 | 9/1981 | Siegmund | 128/6 |
| 4,351,323 | 9/1982 | Ouchi et al. | 128/4 |
| 4,483,326 | 11/1984 | Yamaka et al. | 128/4 |
| 4,620,769 | 11/1986 | Tsuno | 128/6 |
| 4,773,395 | 9/1988 | Suzuki et al. | 128/4 |
| 4,873,965 | 10/1989 | Daniels | 128/6 |
| 4,919,112 | 4/1990 | Siegmund | 128/6 |
| 4,982,725 | 1/1991 | Hibino et al. | 128/4 |
| 4,996,974 | 3/1991 | Ciarlei | 128/4 |
| 5,005,553 | 4/1991 | Aomori | 128/4 |
| 5,025,804 | 6/1991 | Kondo | 128/4 |

FOREIGN PATENT DOCUMENTS 22641 7/1989 Japan .

Primary Examiner—Paul J. Hirsch
Attorney, Agent, or Firm—Armstrong, Westerman, Hattori, McLeland & Naughton

[57] ABSTRACT

A linearizable flexible part which can set a part of a bent insertable section to be linear by the operation of an operating member provided on the base end side of the insertable section is formed in addition to a curvable part formed adjacently to the tip of the flexible elongate insertable section so as to be insertable into such bent body cavity interior as the S-like colon by a simple operation.

17 Claims, 12 Drawing Sheets

FIG.10

FIG.12
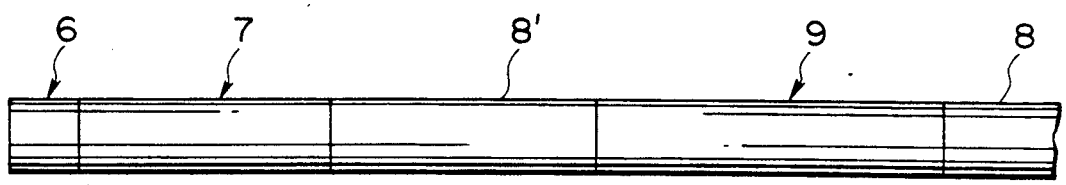
FIG.13
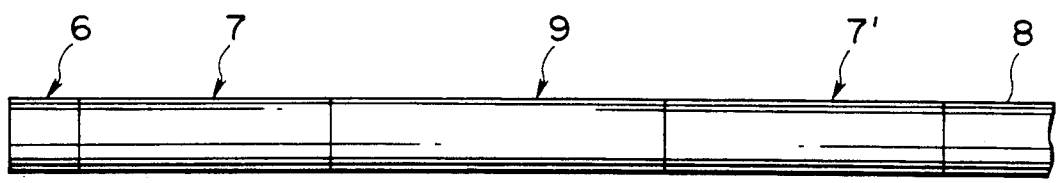
FIG.15
FIG.15a
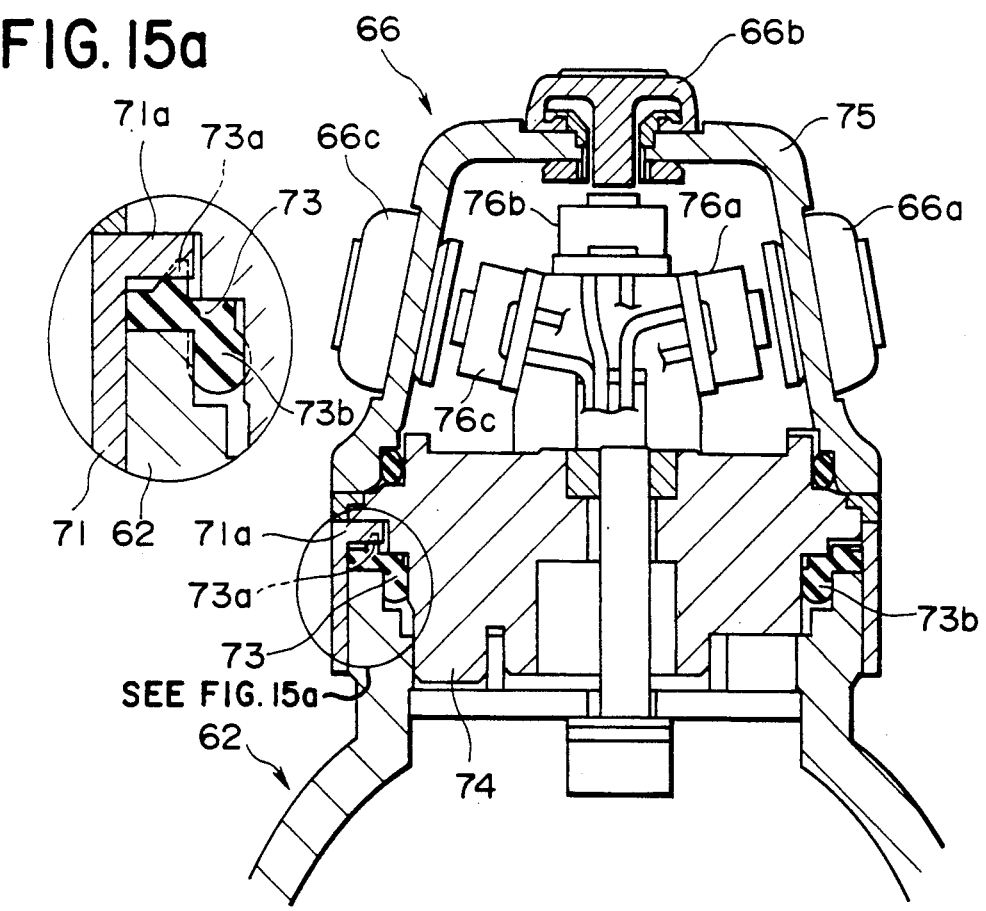

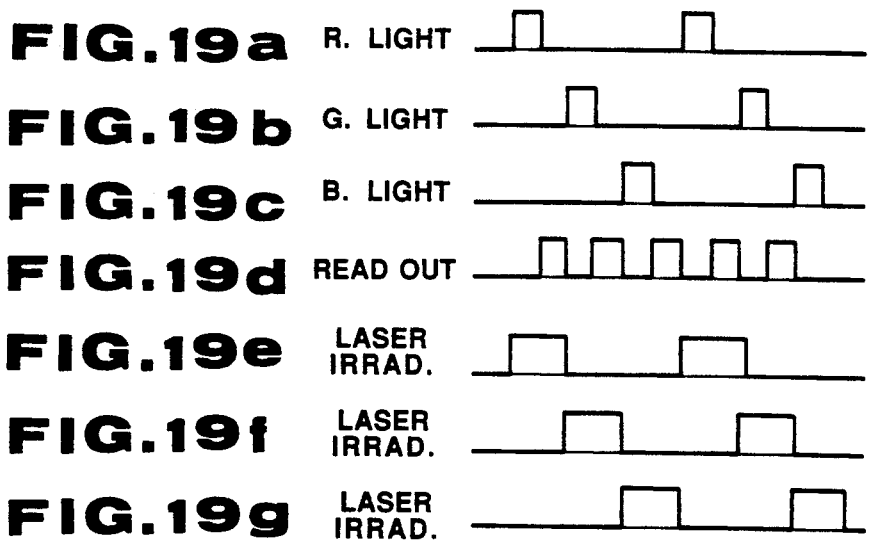
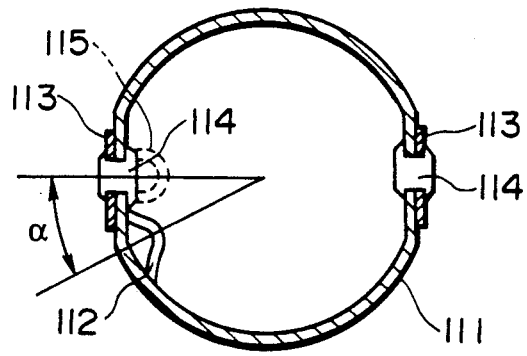

ENDOSCOPE PROVIDED IN THE INSERTABLE SECTION WITH A FLEXIBLE PART WHICH CAN BE MADE LINEAR

BACKGROUND OF THE INVENTION

Field of the Invention and Related Art Statement

This invention relates to an endoscope provided in the insertable section with a flexible part which can be made linear by an operation on the hand base side.

Recently there has come to be extensively used an endoscope whereby a body cavity interior can be observed and, as required, a treating instrument can be inserted to therapeutically treat the body cavity.

The endoscope has a curvable part formed by connecting curvable frames through shafts so that, when an angle wire fixed at the tip to the curvable part at the tip is pulled on the hand base side, the curvable part will be curved. Also, an insertable section flexible tube bendable in any direction is connected to the final frame of the curvable part at the rear end so as to be insertable into bent body cavity.

However, it is difficult or impossible in some case to insert such structure as is mentioned above into such turned and curved organ as the S-like colon part of the large intestine by making the organ linear.

Therefore, in the publication of Japanese utility model application laid open No. 22641/1989, a coil pipe fixed at the rear end within an operating section is fixed at the tip to the tip frame of a second curvable part consisting of curvable frames and shafts in the rear of a first curvable part to give some degree of stiffness to the second curvable part so that, as a result, the part of the second curvable part may be well along the body cavity wall and may help to insert the endoscope.

In the prior art example disclosed in the above mentioned Japanese utility model publication number 22641/1989, in the case of inserting the endoscope over the sharply curved S-like course within the body cavity, as shown in FIG. 1, in the bent part a, the curvable part 202 in the rear of the first curvable part 201 will be well along the body cavity wall and will not obstruct the insertion but, in the bent part b, the flexible tube 203 will not be well along the body cavity wall and will only push the body cavity wall in the direction indicated by the arrow c even if the endoscope is forcibly pushed and there have been defects that not only the endoscope can not be inserted but also a pain is given to the patient.

OBJECTS AND SUMMARY OF THE INVENTION

An object of the present invention is to provide an endoscope which can be smoothly inserted into such bent course as the S-like colon part.

Another object of the present invention is to provide an endoscope applicable to wide uses and high in the insertability.

In the present invention, there are provided a curvable part formed in the rear of the tip forming part of an insertable section and a flexible part which is formed on the hand base side of the above mentioned curvable part and can be made linear so that, in the case of inserting the endoscope into such part in which the insertion is difficult as the S-like colon part, the flexible part may be made linear and easy to smoothly insert.

BRIEF DESCRIPTION OF THE DRAWINGS

FIGS. 2 to 6 relate to the first embodiment of the present invention.

FIG. 2 is a vertically sectioned view showing the structure of the first embodiment.

FIG. 3 is a front view of FIG. 2.

FIG. 4 is a sectioned view on line A—A in FIG. 2.

FIG. 5 is a sectioned view on line B—B in FIG. 2.

FIG. 10 is a vertically sectioned view showing the structure of the fourth embodiment of the present invention.

FIG. 12 is a side view showing an essential part of the fifth embodiment of the present invention.

FIG. 13 is a side view showing an essential part of the sixth embodiment of the present invention.

FIGS. 15 and 15a are a sectioned views showing the structure of a switching part.

FIG. 16b is a sectioned view on line C—C in FIG. 16a.

FIGS. 19a-19g are operation explaining views of FIG. 18.

FIG. 20 is a sectioned view showing a first curvable frame of a curvable part.

DETAILED DESCRIPTION OF THE PREFERRED EMBODIMENTS

Figure 2:
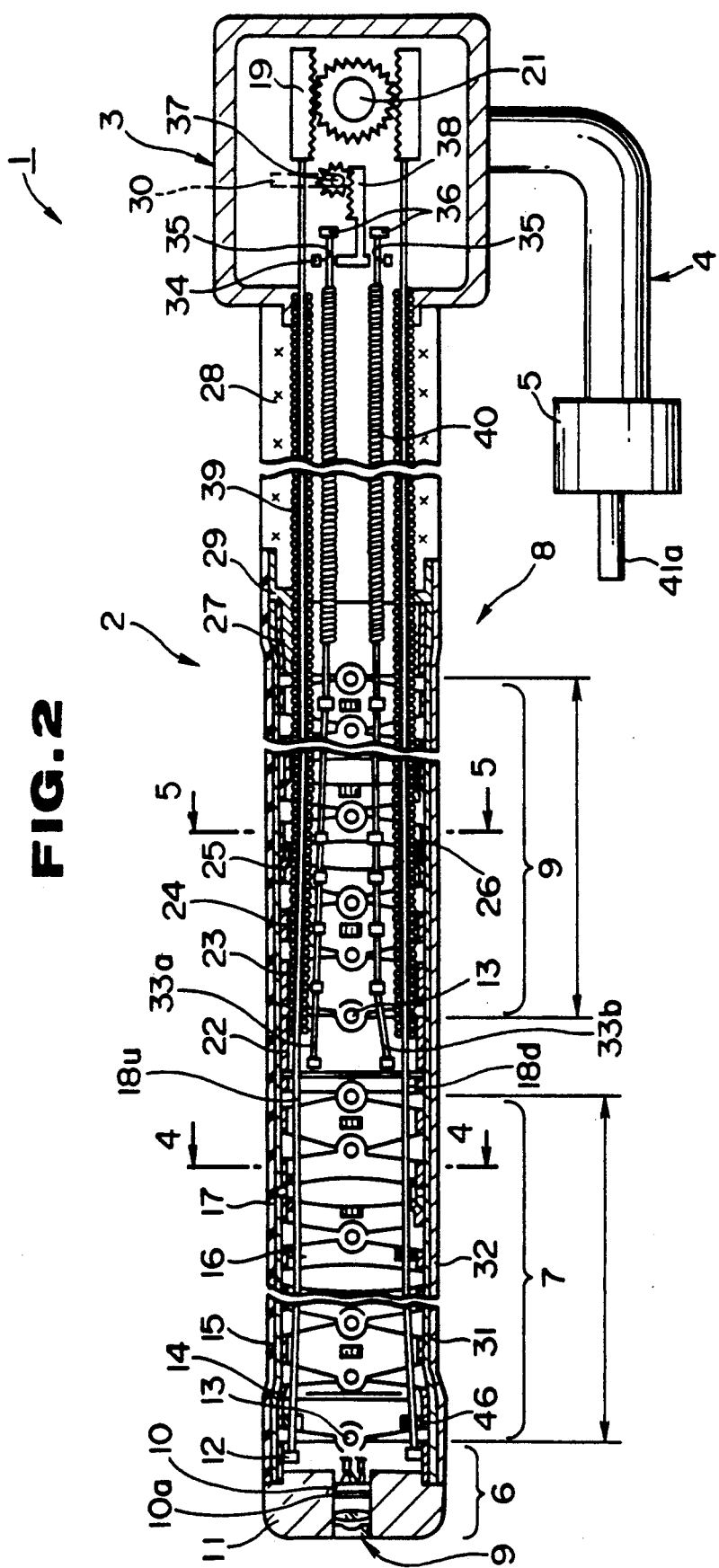

As shown in FIG. 2, the endoscope 1 of the first embodiment comprises an elongate insertable section 2 flexible so as to be insertable into a body cavity or the like, a thick operating section formed at the rear end of this insertable section 2 and a universal cord 4 extended out of the side of this operating section 3. A connector 5 removably connectable to a video processor not illustrated housing a signal processing means for processing signals and a light source means for feeding an illuminating light is fitted to this universal cord 4 at the end.

The above mentioned insertable section 2 comprises a rigid tip forming part 6 formed at the tip (or end) of the above mentioned insertable section 2, a curvable part 7 formed adjacently to this tip forming part 6 and becoming flexible, a flexible part 9 which is formed adjacently to the rear end (or base end) of this curvable part 7 and can be made linear and a flexible tube part 8 extending from the rear end of this flexible part 9 to the front end of the operating section 3.

An objective optical system 9 for forming an optical image of an object to be imaged is fitted in a hole provided in a tip forming member 11 forming the above mentioned tip forming part 6 and a CCD 10 as a solid state imaging device is fitted to its focus position. For example, a mosaic filter 10a is fitted to a photoelectric converting surface of this CCD 10 so as to optically separate colors of respective pixels. The optical image having had the colors separated and formed on the photoelectric converting surface of the CCD 10 is photoelectrically converted to be a signal corresponding to the image and, when a driving signal from a driving signal outputting means within a video processor not illustrated is applied, the corresponding signal will be read out of the CCD 10. When the output signal of the CCD 10 is processed by a signal processing means not illustrated, a standard video signal will be produced to be displayed in a monitor.

A curvable frame (or articulate frame) 12 is secured to the above mentioned tip forming member 11 at the rear end (or base end) and a curvable frame 14 in the next step is connected rotatably in the rightward and leftward directions to the above mentioned curvable frame 12 by rivets 13. In such manner that a curvable frame 15 in the next step is rotatably connected to this curvable frame 14, many curvable frames 16, 17, ... rotatable in two or four directions are connected in the lengthwise direction of the insertable section 2 to form the curvable part 7.

Four curving wires 18u, 18d, 18r and 18l are soldered at the tips in four directions to a curvable frame 12 at the foremost end (in FIG. 2, only the wires 18u and 18d in the upward and downward directions are shown) and are fixed at the rear ends to racks 19 within the operating section 3 and these racks 19 mesh with a pinion 21 connected to an angle knob not illustrated so that, when the angle knob is rotated, a pair of wires 18u and 18d may be advanced or retreated to curve the curvable part upward or downward. The other pair of wires 18r and 18l are also of the same formation. Therefore, by the operation from the operating section 3 side, the curvable part 7 can be freely curved in the four directions of the upward, downward, rightward and leftward directions. The final curvable frame of the curvable part 7 is connected to a ring-like inner mouthpiece 22, the curvable frame 23 is rotatably connected to this inner mouthpiece 22 through the rivet 13 and the curvable frame 24 in the next step is rotatably connected to this curvable frame 23. Thus, in such manner, the same as in the case of the curvable part 7, the curvable frames 23, 24, ... and 27 rotatable in two or four directions are rotatably connected to form a flexible part 9. The final curvable frame 27 of this flexible part 9 is connected with a connecting mouthpiece 29 at the front end of a flexible tube 28.

In both of the above mentioned curvable part 7 and flexible part 9, the curvable frames 12, 14, ... and 27 are coated on the outer periphery with a screen-like blade 31 made of metal wires and the blade 31 is coated further with a rubber tube 32. By the way, the blade 31 is fixed at the front end and rear end respectively to the curvable frames 12 and 27 by soldering and is fixed also with the inner mouthpiece 22 by soldering.

Four linearizing operation wires (briefly mentioned as linearizing wires hereinafter) 33a, 33b, 33c and 33d are soldered at the tips in substantially upward, downward, rightward and leftward directions to the above mentioned inner mouthpiece 22 (in FIG. 2, only the linearizing wires 33a and 33b in the upward and downward directions are shown) and are bonded at the rear ends through holes 35 formed in an engaging member 34 for linearizing within the operating section 3 to stopper members 36 of diameters larger than of the above mentioned holes 35 so as not to be pulled out of the holes 35. Also, as shown in FIG. 2, usually the stopper member 36 and engaging member 34 are kept at such sufficient distance between them that, even if the flexible part 9 curves in any of the four directions, the stopper member 36 will not contact the engaging member 34. That is to say, the stopper member 36 and engaging member 34 are usually disengaged with each other so that the flexible part 9 may be bent without being restricted by the flexible part 9 and linearizing wires 33a and 33b.

The above mentioned engaging member 34 is provided with a rack 38 meshing with a pinion 37 connected to a linearizing knob 30 so that, by the operation of rotating the linearizing knob 30, the pinion 37 may be simultaneously rotated and, by this rotation, the engaging member 34 together with the rack 38 may be moved rearward. When this engaging member 34 is moved rearward, it will engage with the stopper member 36 and, when it is further moved rearward, this stopper member 36 will be pushed, the linearizing wires 33a, 33b, 33c and 33d will be pulled rearward, will get a pulling force and will be tensioned and the curvable frames 23, 24, ... and 27 will also get a pulling force and will be tensioned so that the flexible part 9 may be made linear.

In this case, by varying the rotating amount (or angle) of rotating the linearizing knob 30, the pulling force given to the linearizing wires 33a, 33b, 33c and 33d can be varied and the driving force linearening the flexible part 9 can be adjusted.

Now, the curving operation wires 18u, 18d, 18r and 18l inserted through the insertable section 2 are inserted respectively through guide coils 39 within the flexible tube 28 and flexible part 9 so as to be protected and the above mentioned guide coils 39 are fixed at the tips to the inner mouthpiece 22 and at the rear ends within the operating section 3. That is to say, the guide coils 39 guide the curving operation wires 18u, 18d, 18r and 18l from the base end of the insertable section 2 to the interior of the flexible part 9 and are fixed at the tips to the inner mouthpiece 22.

Also, the linearizing wires 33a, 33b, 33c and 33d are protected by guide members 40 within the flexible tube 28 and these guide members 40 are fixed at the tips to the connecting mouthpiece 29 and at the rear end within the operating section 3. That is to say, the guide members 40 guide the linearizing wires 33a, 33b, 33c and 33d from the base end of the insertable section 2 to a position a little before the front end of the flexible tube 28 and are fixed at the tips to the connecting mouthpiece 29.

Figure 4:
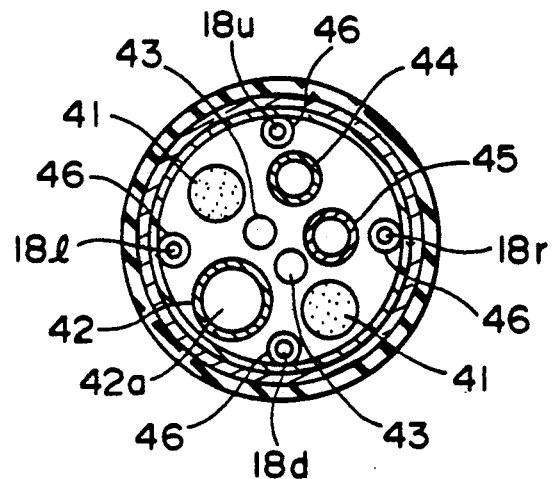

These guide coils 39 and guide members 40 are free in the diametral direction except in the fixing parts at both ends, can enter other contents and do not become large in the diameter. In fact, as shown in FIG. 4, there are inserted through the above mentioned insertable section 2 not only the wires 18u, 18d, 18r and 18l but also two light guides 41 transmitting illuminating lights and emitting them toward a front object from the tip surface, a channel tube 42 forming a channel 42a for passing a treating instrument, signal transmitting cables 43, an air feeding tube 44 and a water feeding tube 45.

The above mentioned light guides 41 are inserted through the insertable section 2 and also through the universal cord 4 extended out of the side of the operating section 3 and lead to a light guide connector 41a from the connector 5. By fitting this light guide connector 41a to a light source apparatus not illustrated, an illuminating light is fed from the light source apparatus. This illuminating light is transmitted and is emitted toward the front object from the tip surface fixed to the tip 6.

Figure 3:
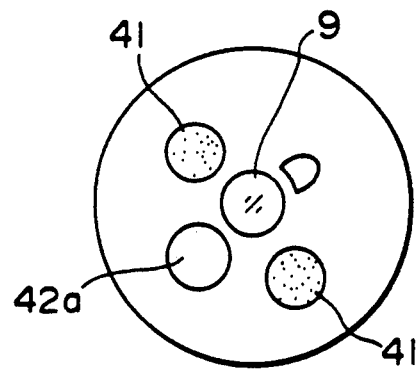

The above mentioned air feeding tube 44 and water feeding tube 45 join with each other within the tip forming member 11 to become one tube leading at the tip to a nozzle opposed to the outer surface of the objective optical system 9 as shown in FIG. 3. A body liquid or the like deposited on the surface of the objective optical system 9 can be removed by water or gas jetted out of this nozzle.

Figure 5:
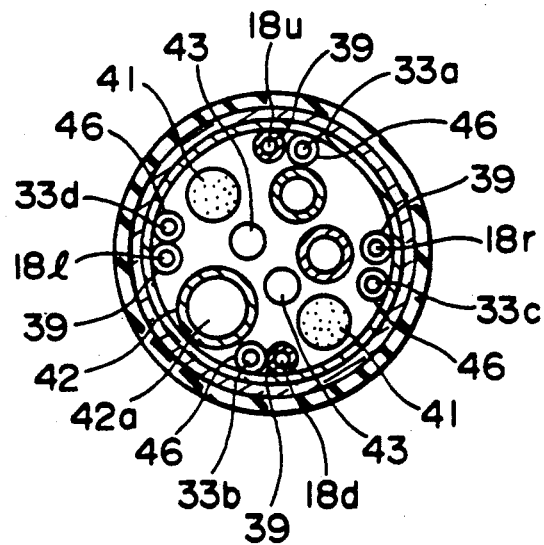

Further, the wires 33a, 33b, 33c and 33d are inserted through the part of FIG. 5 shown in the cross-section on line B—B.

By the way, the wire 18u etc. and wire 33a etc. are guided by a wire receptacle 46 in the positions through which they are to be inserted so that, even if they are curved or the like, the positions through which they are to be inserted may not deviate.

By the way, the length of the flexible part 9 is set, for example, to be 35 to 45 cm.

The hardness of the rubber tube 32 covering the curvable part 7 and flexible part 9 is higher in the flexible part 9 than in the curvable part 7. For example, the hardness is 45° in the curvable part 7 and is 70° in the flexible part 9. The thickness is different in the curvable part 7 and flexible part 9. For example, it is set to be 0.5 mm in the curvable part 7 and 0.7 mm in the flexible part 9.

The operation of the thus formed first embodiment shall be explained in the following with reference to the using example in FIG. 6.

Figure 6A:
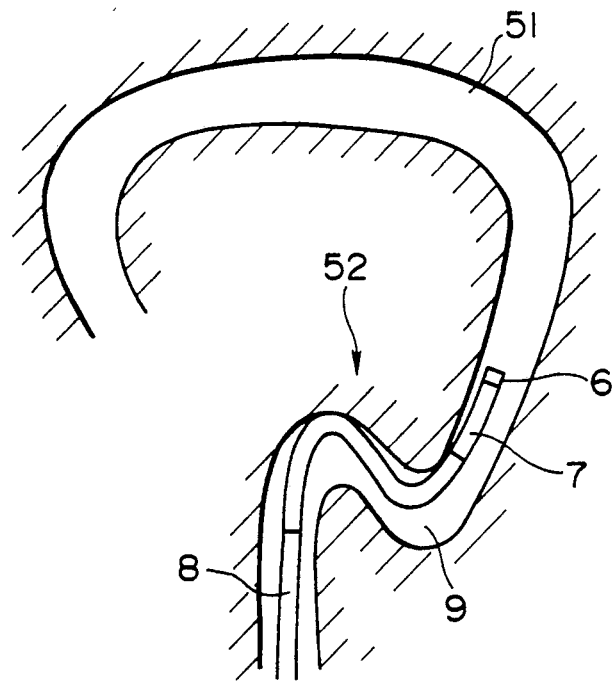
FIGS 6a and 6b are operation explaining views of the first embodiment.
Figure 6B:
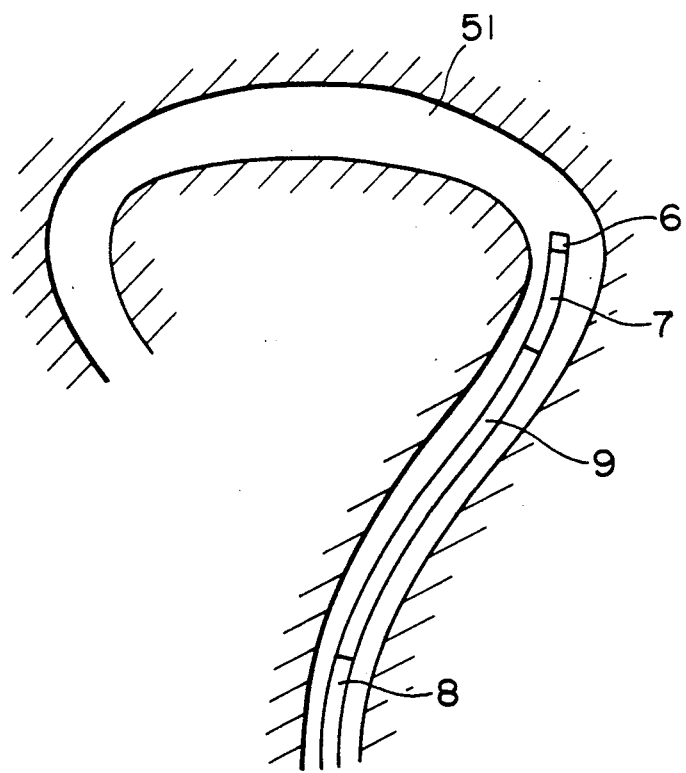

As shown, for example, in FIG. 6a, in the case of inserting the insertable section 2 of the endoscope 1 into the deep side of such body cavity 51 as the large intestine, if the curvable part 7 on the tip side of the insertable section 2 is curved and is inserted into the deep side in response to the bend of such S-like bent part 52 as the S-like colon part of the body cavity 51 as in this drawing, as shown in this FIG. 6a, when the tip side can be inserted into the deep part of this S-like bent part 52 but the flexible part 9 in the rear of the curvable pat 7 contacts the steep bent part of the S-like bent part 52, even if the insertable part 2 is pushed forward as it is, the contacted inside wall will be only pushed and the insertion will be difficult. However, in this first embodiment, when the linearizing knob 30 is operated, the wires 33a, 33b, 33c and 33d are pulled and the flexible part 9 is made linear, the S-like bent part 52 will be also made linear to be as shown in FIG. 6b. In this state, when the insertable section is paid out forward, it will be able to be smoothly inserted into the deep side.

According to this first embodiment, as the flexible part 9 which can be linearized by the operation of the linearizing knob 30 as an operating means on the hand base side is provided in the rear part (base end side) of the curvable part 7, the linearizing operation will be made even within the S-like bent body and the insertable section will be able to be easily inserted. Even in the case of inserting the insertable section into another body cavity than the S-like colon part, by carrying out the same operation, it can be smoothly inserted and the burden on the operator will be able to be reduced. Therefore, this first embodiment is an endoscope applicable to wide uses and high in the insertability.

Figure 1:
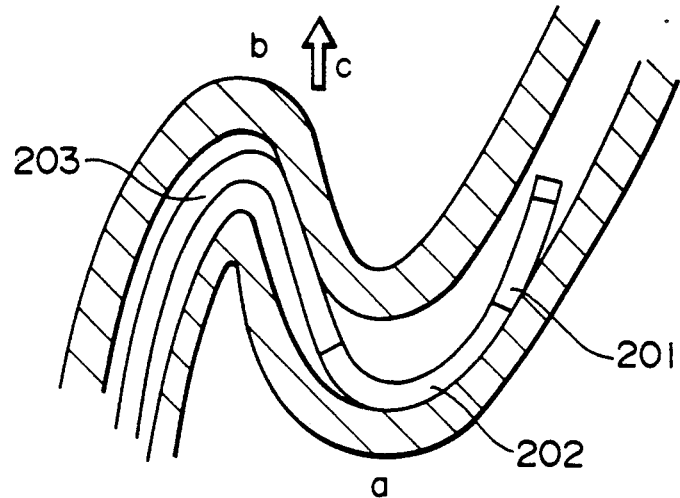
FIG. 1 is an explanatory view for explaining the defects of a prior art example.
Figure 7:
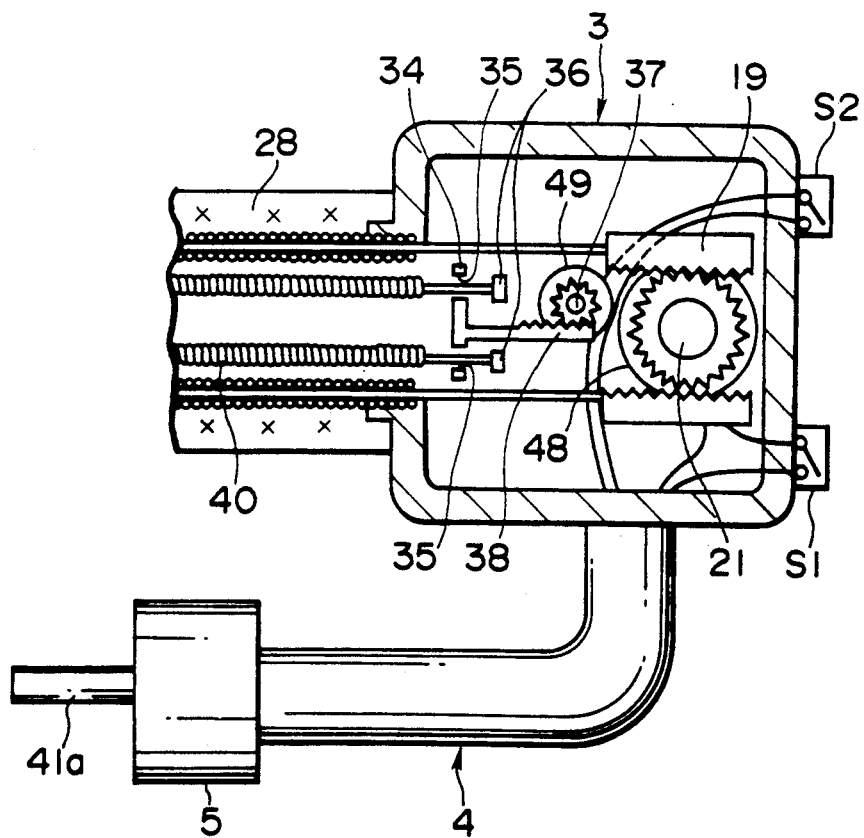
FIG. 7 is a sectioned view showing an essential part of a modification of the first embodiment of the present invention.

In the above mentioned first embodiment, by manually rotating the angle knob and linearizing knob 30, the respective pinions 21 and 37 are rotated for curving and linearizing. However, as in the modification shown in FIG. 7, motors 48 and 49 may be built-in within the operating section 3, switches S1 and S2 switching on/off the feed of electric power to these motors 48 and 49 may be provided, for example, on the outer surface of the operating section 3 and the respective pinions 21 and 37 may be rotated by the torques of the respective motors 48 and 49.

Figure 8:
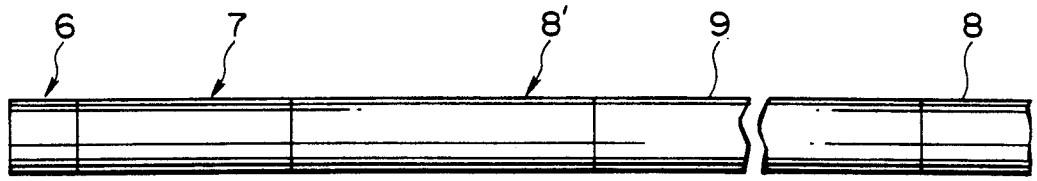
FIG. 8 is a side view showing an essential part of the second embodiment of the present invention.

FIG. 8 shows the the tip side of the insertable section 2 in the second embodiment of the present invention.

In this second embodiment, a flexible tube part 8' is formed between the curvable part 7 and linearizable flexible part 9 in the above mentioned firs embodiment. This flexible tube part 8' is, for example, about 10 cm long. The others are of the same formation as of the first embodiment and its operation and effects are the same as of the first embodiment.

Figure 9:
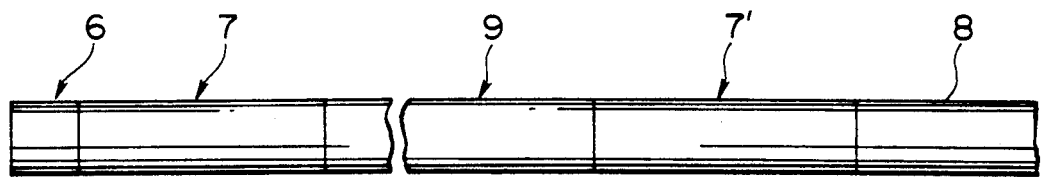
FIG. 9 is a side view showing an essential part of the third embodiment of the present invention.

FIG. 9 shows the formation of the tip side of the insertable section 2 in the third embodiment of the present invention.

In this third embodiment, a second curvable part 7' is provided between the linearizable flexible part 9 and flexible tube part 8 in the first embodiment. The length of this second curvable part 7' is, for example, 80 cm. The other formations are the same as of the first embodiment and the operation and effects are also substantially the same as of the first embodiment.

Figure 10:
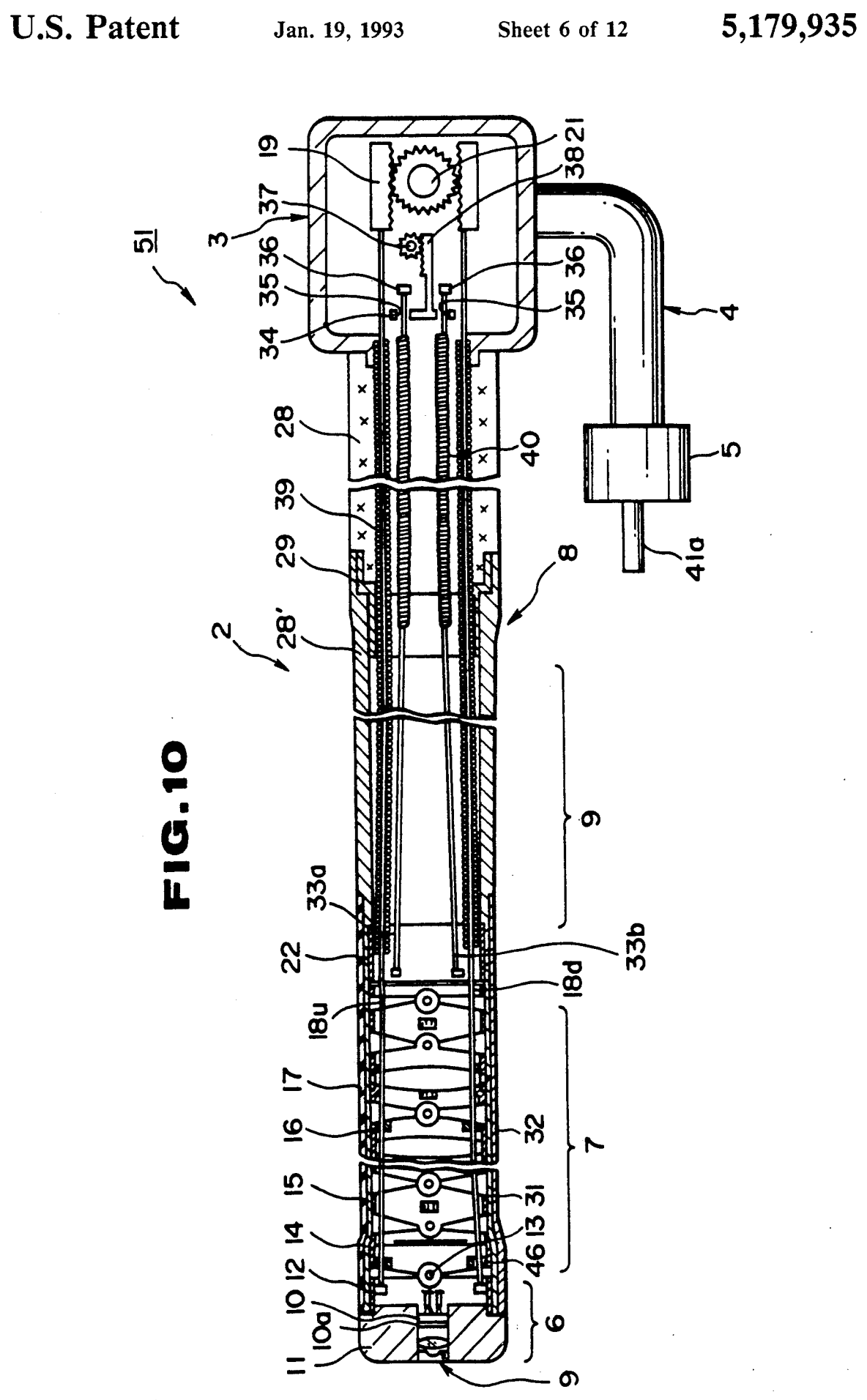

FIG. 10 shows the formation of an endoscope 51 of the fourth embodiment of the present invention.

In the endoscope 1 of the first embodiment, the linearizable flexible part 9 is formed by using the curvable frames 23, 24, 25, . . . and 27, blade 31 and rubber tube 32 but, in the endoscope 51 of this fourth embodiment, the linearizable flexible part 9 is of the same formation as of the flexible tube part 8. That is to say, this linearizable flexible part 9 is made to be of a hose-like structure from the curvable tube-like structure and the flexible part 9 is coated with a flexible tube 28'. This flexible tube 28' is fixed at the tip to the inner mouthpiece 22 and at the rear end to the connecting mouthpiece 29.

The curving wires 18u, . . . protected by the guide coils 39 the same as in the first embodiment and the linearizing wires 33a, . . . not coated with the guide members 40 are inserted through the inside of the above mentioned flexible tube 28'.. In this embodiment, the linearizing wires 33a . . . within the flexible tube 28' are not guided by the wire receptacle 46. The other formations are the same as in the first embodiment. This embodiment has the same effects as of the first embodiment and can obtain the same operation and effects with a formation simpler than of the first embodiment.

Figure 11:
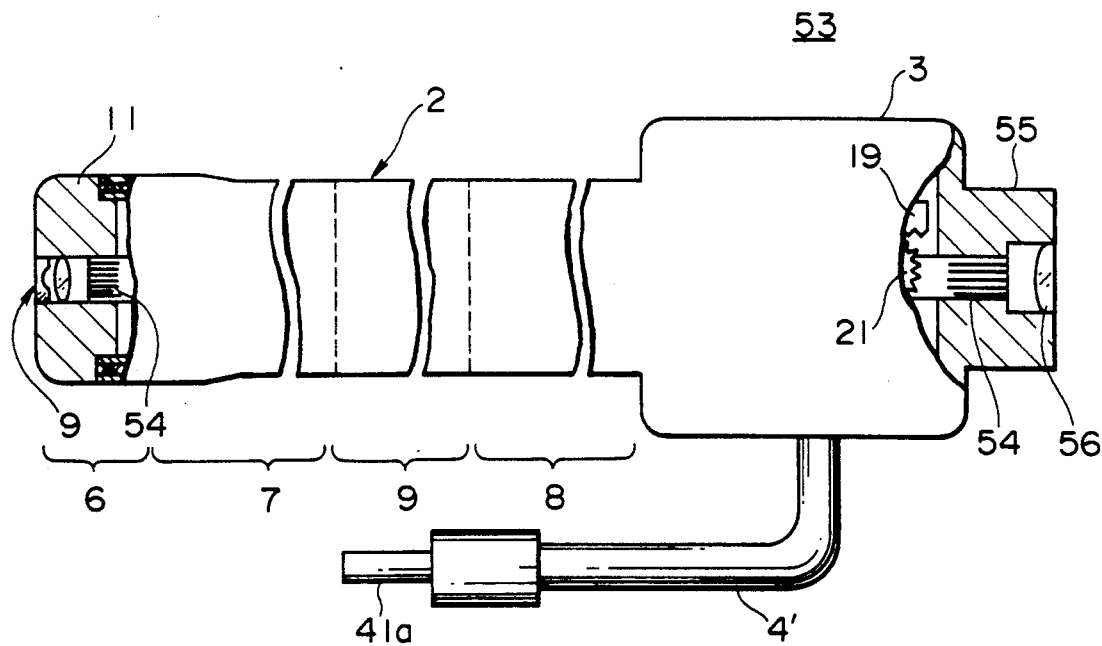
FIG. 11 is a side view showing a modification of of the fourth embodiment of the present invention.

FIG. 11 shows a fiber scope 53 as a modification of the fourth embodiment of the present invention.

In this fiber scope 53, the tip surface of an image guide 54 formed of a fiber bundle transmitting an optical image is arranged in the image forming position of the objective optical system 9 and the optical image is transmitted to the other end surface on the eyepiece part 55 side formed at the rear end of the operating section 3 by the image guide 54 inserted through the insertable section 2 so that the optical image transmitted through the eyepiece lens 56 arranged opposite the other end surface may be observed with a naked eye. As this fiber scope 53 has no CCD 10, not the signal transmitting cable but a light guide (not illustrated) is inserted through the cord 4' extended out of the light guide. The other formations are the same as in the fourth embodiment. The effects are also substantially the same.

FIG. 12 shows the formation of the tip side of the insertable section 2 in the fifth embodiment of the present invention.

In this fifth embodiment, a second flexible tube part 8' is provided between the curvable part 7 and linearizable flexible part 9 in the fourth embodiment. The other formations are the same as in the fourth embodiment. The operation and effects are also substantially the same as of the fourth embodiment.

FIG. 13 shows the formation of the tip side of the insertable section 2 in the sixth embodiment of the present invention.

In this sixth embodiment, a second curvable part 7' is provided between the linearizable flexible part 9 and the flexible tube part 8 in the fourth embodiment. The other formations are the same as in the fourth embodiment. The operation and effects are also substantially the same as in the fourth embodiment.

Different embodiments can be formed by combining the above described respective embodiments and modifications and also belong to the present invention.

Figure 14A:
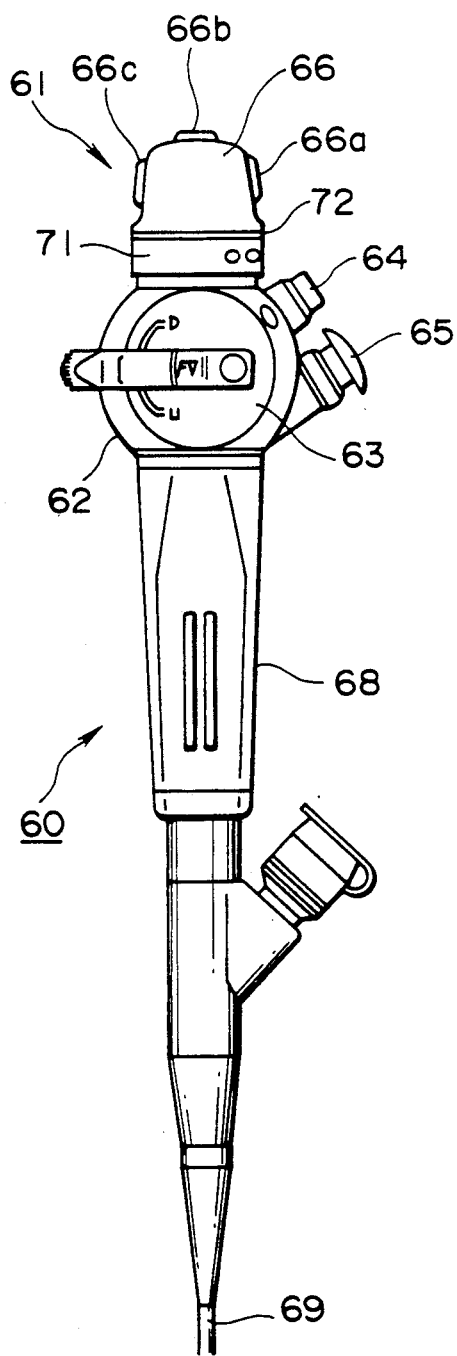
FIGS. 14a and 14b are side views showing the periphery of an operating section of an electronic endoscope.
Figure 14B:
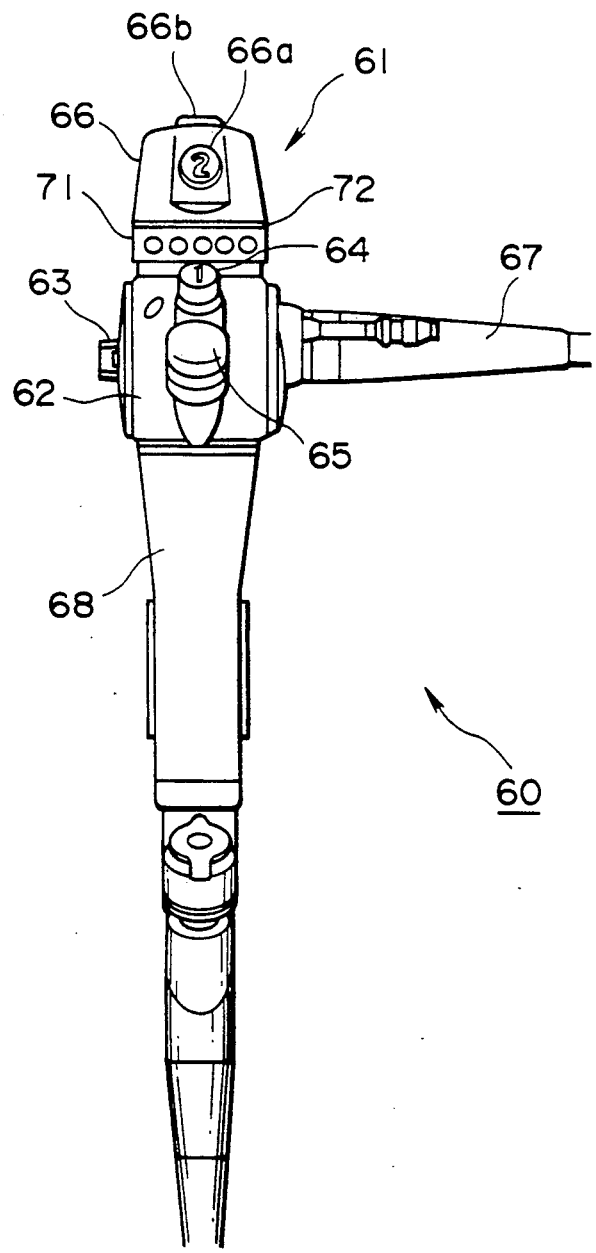

Now, an electronic endoscope 60 shown in FIGS. 14a and 14b is provided on the side of an operating section body 62 forming an operating section 61 with an angle knob 63, on the periphery of it with a switching part 64 and air and water feeding button 65 and on the top side with a switching part 66 having key tops 66a, 66b and 66c. Also, a universal cord 67 is extended out of the side opposite the angle knob 63.

A gripping part 68 is formed below the operating section body 62 and an insertable section 69 is formed further below the gripping part 68.

Between the above mentioned operating section body 62 and switching part 66 is fitted a name plate 71 as prevented by a fixing member 72 from being pulled out.

As shown in FIG. 15, against a projecting piece 71a projecting on the inside in the radial direction of the name plate 71, by a name plate energizing part 73a (See the magnified view) of a different shaped O-ring 73 inside the projecting piece 71a, the name plate 71 is energized upward and outward and the projecting piece 71a of the name plate 71 is pushed against a switch cover receptacle 74 to positively fix the name plate 71. This different shaped O-ring 73 retains a water-tightening function with a spherical part 73b (See the magnified view 15a) between the operating section body 62 and switch cover receptacle 74.

That is to say, as the different shaped O-ring 73 has both of the water-tightening function and the name plate 71 energizing function, the number of component parts can be reduced and the assemblability can be improved.

By the way, a switch cover 75 is water-tightly fitted through an O-ring on the upper side of the switch cover receptacle 74. Key tops 66a, 66b and 66c are fitted, for example, to three parts of this switch cover 75 and switches 76a, 76b and 76c are respectively fitted inside them.

By the way, in the magnified view 15a of FIG. 15, the shape of the different shaped O-ring 73 before being fitted is shown by a broken line.

Figure 16A:
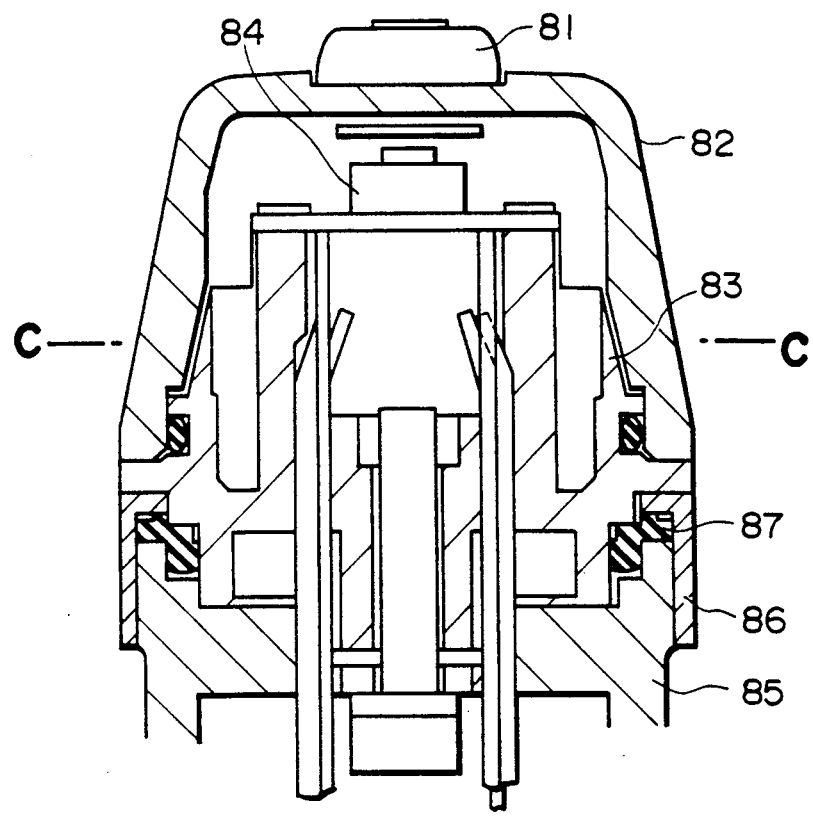
FIG. 16a is a schematic sectioned view of another switching part in FIG. 14.
Figure 16B:
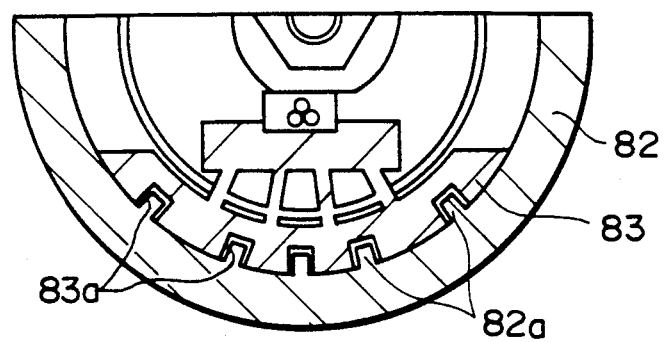

Also, as shown, for example, in FIG. 16a, in case a switch cover 82 provided with a key top 81 is to be fitted to a switch cover 83, as shown in FIG. 16b, a plurality of convex parts 82a are provided on the inner peripheral surface of the switch cover 82 and, on the other hand, a plurality of concave parts 83a fitting the above mentioned convex parts 82a are provided on the outer peripheral surface of a switch cover receptacle 83 so that the bonding area in bonding and fixing these convex and concave parts with a bonding agent may be wide and the switch cover 82 may be strongly fixed.

. By the way, a switch 84 is provided inside the key top 81. The same as in FIG. 15, a water-tightening O-ring is interposed between the switch cover 82 and switch cover receptacle 83 and a different shaped O-ring 87 is interposed between an operating section body 85 and a name plate 86.

Figure 17:
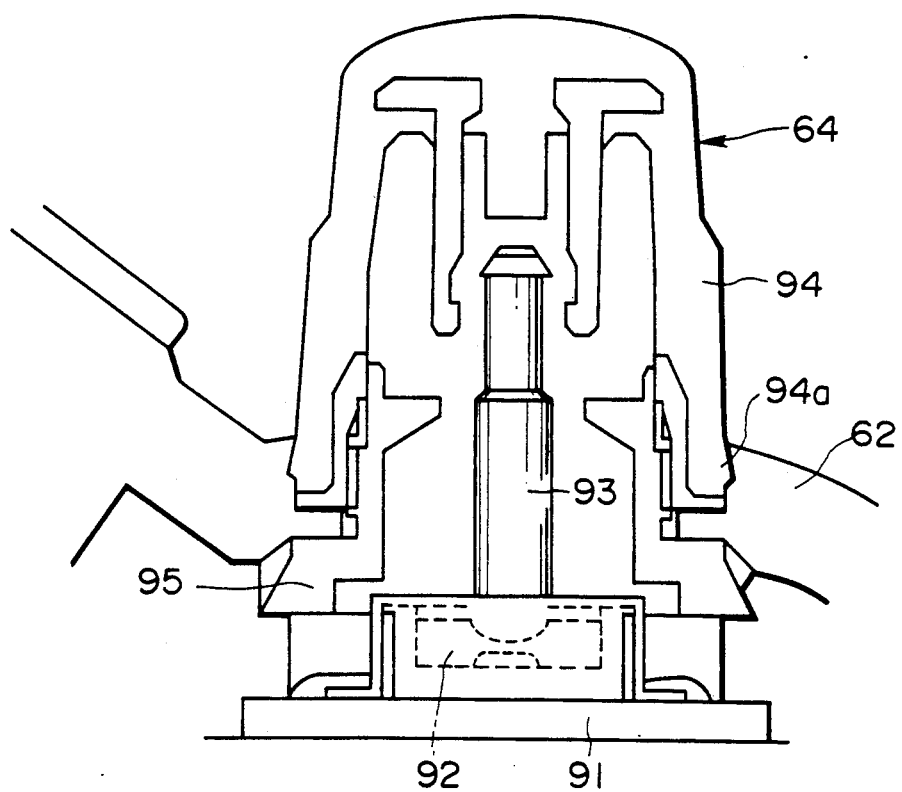
FIG. 17 is a schematic explanatory view showing the structure of the switching part in FIG. 14.

Also, the structure of the switching part 64, for example, in FIG. 14 is as in FIG. 17.

As shown in this drawing, a switch 92 is fitted to a base plate 91. A stem 93 forming the switch 92 is projected upward and is covered with a cup-like rubber member 94 so that, even if it is pushed from the upward and horizontal (diagonal) directions, the stem 93 may move downward at the lower end to be switched on.

A fitting member 95 fixed to the opening of the operating section body 62 is symmetrical in the rotation so that the rubber member 94 may be easily fitted through this fitting member 95. A projecting part 94a is provided over the entire periphery of the rubber member 94 so that, in assembling with the fitting member 95, water-tightness may be secured with the opening wall surface of the operating section body 62 pressed in contact with this projecting part 94a.

Figure 18:
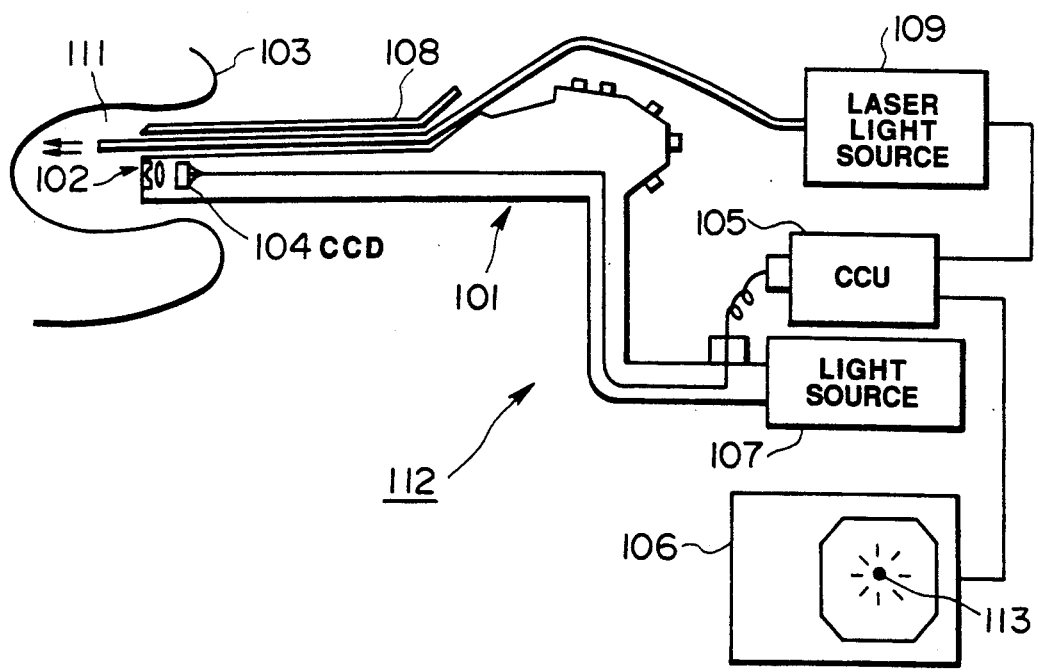
FIG. 18 is a formation view showing an endoscope variable in the laser guide light color.

FIG. 18 shows a laser light color variable endoscope 101.

An optical image of an object 103 to be imaged is formed on a CCD 104 by an objective lens 102 provided at the tip of this endoscope 101 and is photoelectricallly converted to a signal, the signal is input into a CAU 105 and is processed and an endoscope image is displayed in a monitor 6.

A light source 107 sequentially emits R, G and B lights as shown in FIGS. 19a, 19b and 19c and illuminates the object 103 through a light guide not illustrated. A fiber bundle 111 leading a laser light from a laser light source 109 is inserted through a channel 108 of the endoscope 101 and emits the laser light from the tip surface. In this imaging system 112, as shown in FIG. 19d, after the R, G and B lights are radiated, a CCD driving signal (reading signal) is output and an image signal accumulated in the CCD 104 is read out. However, for example, if the laser guide light from the laser light source 109 is radiated as synchronized with the R, G and B lights as shown in FIGS. 19e, 19f and 19g, a radiated spot light 113 on the monitor picture will be displayed in red, green and blue colors. If FIGS. 19e, 19f and 19g are combined, the spot light will be able to be displayed in any color.

That is to say, by varying the laser guide light radiating timing, the spot light 113 on the monitor picture can be displayed in any color.

Therefore, it is usefull to vary with various informations the spot light (guide light) displayed in the monitor 106.

Examples of varying the spot light with various informations may be utilized, for example:
1) To express the laser output with the variation of the color;
2) To express the laser radiating time with the variation of the color;
3) To express the laser radiating energy with the variation of the color;
4) To express the distance to the object with the variation of the color; and for others.

FIG. 20 shows a first (tip) curvable frame 111 forming a curvable part. Conventionally, it has been designed that there should be no lag in the rotating direction between the wire receptacle within the curvable part and the wire fixing part in the first curvable frame but, in FIG. 20, the wire fixing part 112, for example, in the R and L directions of the first curvable frame 111 is provided to lag, for example, by an angle α in a position not interfering with the articulate shaft (curvable shaft) 114 of the first pin 113. By the way, a wire receptacle 115 is shown by broken lines.

Thereby it can be seen that, in the conventional example, for example, when the wire for the R and L directions is passed through the wire receptacle from the rear end side of the curvable part, in case the wire is to be inserted into the last wire fixing part of the first curvable part, the wire will catch on the head of the articulate shaft of the first pen and the wire assembling operatability will not be good.

FIG. 21 shows a wire guide member.

In the conventional example, a part of the curvable frame is formed to be concave in the axial direction and a wire is inserted through the concave part. However, in such case, there have been defects that, in producing the frame, a precise press work is necessary and the cost is high. Therefore, as in FIG. 21, the cost can be reduced.

Figure 21A:
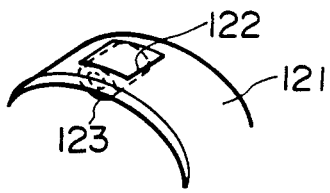
FIGS. 21a-21g explanatory views showing the structure of a wire receptacle fixing part.
Figure 21B:
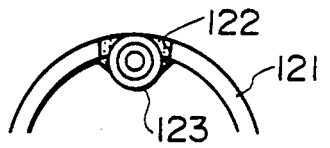
Figure 21C:
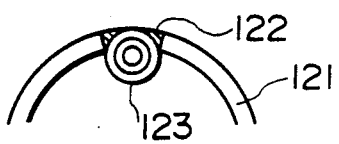
Figure 21D:
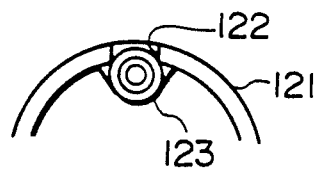
Figure 21E:
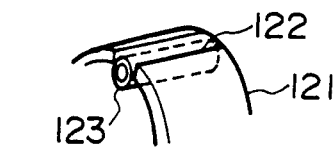
Figure 21F:
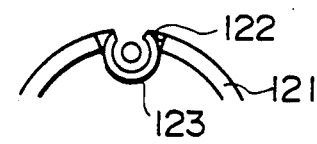
Figure 21G:
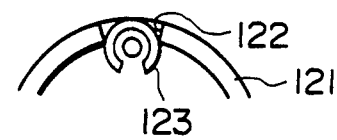
Figure 22:
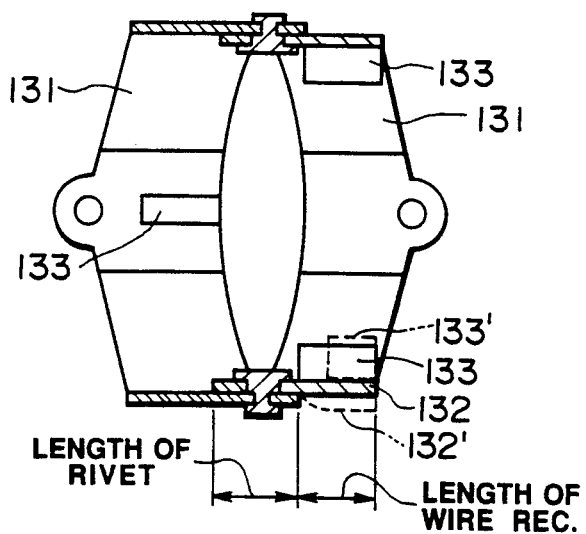
FIG. 22 is a sectioned view showing a curvable frame provided with a wire receptacle.

As shown in FIG. 21a, for example, a square incision 122 is made in a (curvable) frame 121 and, as shown in FIG. 21b, a ring-like guide member 123 is secured as by soldering on the inner peripheral side of the frame 121. In this case, as shown in FIG. 21c, the incision 122 may be made in a shape properly fitting the guide member 123. Thereby, the positioning will be simple and the assembly will be easy. Also, as shown in FIG. 21d, the frame 121 may be made thicker than the guide member 123 so that the inner cavity may be expanded and the diameter may be made small. Also, as shown in FIG. 21e, the incision 122 may be provided over the entire length in the axial direction of the frame 121 so as to secure a pipe-like guide member 123. (By the way, in this case, if the wire is not displaced from the guide member 123, as shown in FIG. 21f or 21g, the guide member 123 may be partly incised.) FIG. 22 shows a curvable frame 131 in the curvable part in which the wire receptacle can be made longer.

Conventionally, the curvable frame and wire receptacle have been secured by soldering on an arc of the inner peripheral surface avoiding the throttled part of the ear part for connecting with the adjacent curvable frame. In such case, there is a relation of "Length in the axial direction = Ear part + Press working margin + Wire receptacle" in the part on the curvable frame to which the wire receptacle is secured. In case the length in the axial direction is determined to be a predetermined length, the diameter of the ear part can not be easily made small and the wire receptacle can not help being made short and therefore will be severely worn but, in FIG. 22, the ear part is not pressed but all in the lengthwise direction is pressed and, without providing the press working margin in the lengthwise direction, a plane pressed part 132 is formed to secure the wire receptacle 133. Thereby, the press working margin can be omitted and the wire receptacle can be made long without being influenced by the diameter of the ear part of the adjacent articulate frame. By the way, for the sake of comparison, the broken lines show a press worked part 132 and wire receptacle 133'.

What is claimed is:

1. An endoscope, comprising:
   a flexible elongate insertable section insertable into a body cavity or the like, said insertable section having a terminal end which includes a rigid tip;
   a light guide inserted through said insertable section and transmitting an illuminating light fed to one end surface and emitting it from the end surface at said terminal end of said insertable section;
   an objective optical system provided at said rigid tip at said terminal end of said insertable section and forming an image of an object to be imaged;
   a curvable part formed on a base end side of said rigid tip of said insertable section; and
   a linearizable flexible part formed on a base end side of said curvable part of said insertable section and settable to be linear by the operation of an operating means provided on a base end side of said insertable section.

2. An endoscope according to claim 1 which is an electronic scope having a solid state imaging device having a photoelectric converting function arranged in the image forming position of said objective optical system.

3. An endoscope according to claim 1 which is a fiber scope having a flexible image guide fiber bundle transmitting an optical image arranged in the image forming position of said objective optical system.

4. An endoscope according to claim 1 wherein said curvable part is formed adjacently to said rigid tip at the base end of said tip.

5. An endoscope according to claim 4 wherein said linearizable flexible part is formed adjacently to said curvable part at the base end of said curvable part.

6. An endoscope according to claim 4 wherein said linearizable flexible part is formed adjacently to the base end of a flexible part which in turn is formed adjacently to the base end of said curvable part.

7. An endoscope according to claim 5 wherein a second curvable part is formed adjacently to the base end of said linearizable flexible part.

8. An endoscope according to claim 1 wherein said operating means is provided in an operating section formed as connected to said insertable section at the base end.

9. An endoscope according to claim 1 wherein said linearizable flexible part comprises a plurality of articulate frames housed as rotatably connected with each other within a flexible tube forming said curvable part and at least one pair of linearizing operation wires fixed at one end on the tip side of said plurality of articulate frames and engaged at the other end with said operating means.

10. An endoscope according to claim 1 wherein said linearizable flexible part comprises a flexible tube and at least one pair of linearizing operation wires fixed at one end on the tip side of said flexible tube and engaged at the other end with said operating means.

11. An endoscope according to claim 9 or 10 wherein said operating means is a wire relaxing tensioning operation means selectively relaxing and tensioning said linearizing operation wires.

12. An endoscope according to claim 11 wherein said wire tensioning relaxing operation means comprises a moving means for moving said linearizing operation wires in a direction from the base end side of said insertable section to cause a condition of said linearizing operation wires to be changed from a disengaged free state to a tensioned state.

13. An endoscope according to claim 12 wherein said moving means has a rack provided with engageable and disengageable projections at the base ends of said linearizing operation wires and a pinion rotating in engagement with said rack to move said rack.

14. An endoscope according to claim 13 wherein said moving means further comprises a knob for manually rotating said pinion.

15. An endoscope according to claim 13 wherein said moving means further comprises a motor rotating and driving said pinion and a switch for switching on/off the rotating operation of said motor.

16. An endoscope according to claim 1 wherein said operating means has a linearizing force varying function which can vary the driving force setting said linearizable flexible part to be linear.

17. An endoscope according to claim 13 wherein the driving force setting said linearizable flexible part to be linear through said linearizing operation wires can be varied by varying the rotation amount rotating said pinion.

* * * * *